(12) United States Patent
Myntti et al.

(10) Patent No.: US 7,976,873 B2
(45) Date of Patent: *Jul. 12, 2011

(54) EXTRACELLULAR POLYSACCHARIDE SOLVATING SYSTEM FOR TREATMENT OF BACTERIAL EAR CONDITIONS

(75) Inventors: Matthew F. Myntti, St. Augustine, FL (US); Dana A. Oliver, Jacksonville, FL (US); Cecil O. Lewis, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 18 days.

This patent is subject to a terminal disclaimer.

(21) Appl. No.: 11/739,508

(22) Filed: Apr. 24, 2007

(65) Prior Publication Data

US 2007/0264353 A1 Nov. 15, 2007

Related U.S. Application Data

(63) Continuation-in-part of application No. 11/431,495, filed on May 10, 2006, now abandoned.

(51) Int. Cl.
*A61K 33/00* (2006.01)
*A61K 33/06* (2006.01)
*A61K 33/26* (2006.01)

(52) U.S. Cl. ........ 424/600; 424/646; 424/682; 424/70.1
(58) Field of Classification Search .......... None
See application file for complete search history.

(56) References Cited

U.S. PATENT DOCUMENTS

| | | | |
|---|---|---|---|
| 3,422,186 A | 1/1969 | Sasmor |
| 4,002,775 A | 1/1977 | Kabara |
| 4,107,328 A | 8/1978 | Michaels |
| 4,851,521 A | 7/1989 | Della Valle et al. |
| 5,017,229 A | 5/1991 | Burns et al. |
| 5,166,331 A | 11/1992 | Della Valle et al. |
| 5,208,257 A | 5/1993 | Kabara |
| 5,229,103 A | 7/1993 | Eagle et al. |
| 5,246,964 A | 9/1993 | Ueno |
| 5,290,552 A | 3/1994 | Sierra et al. |
| 5,326,567 A | 7/1994 | Capelli |
| 5,336,163 A | 8/1994 | DeMane et al. |
| 5,442,053 A | 8/1995 | Della Valle et al. |
| 5,480,658 A | 1/1996 | Melman |
| 5,575,815 A | 11/1996 | Slepian et al. |
| 5,601,594 A | 2/1997 | Best |

(Continued)

FOREIGN PATENT DOCUMENTS

EP 0 530 861 B1 3/1993

(Continued)

OTHER PUBLICATIONS

Post, J.C., "Direct evidence of bacterial biofilms in otitis media", Laryngoscope 111(12):2083-94 (2001).

(Continued)

*Primary Examiner* — David J Blanchard
*Assistant Examiner* — Suzanne Ziska
(74) *Attorney, Agent, or Firm* — IPLM Group, P.A.

(57) ABSTRACT

Chronic otitis media and other bacterial ear conditions may be treated by applying a solvating system containing a metal ion sequestering agent and surfactant to a bacterial biofilm in the middle or inner ear. The solvating system disrupts the biofilm and aids in its removal.

46 Claims, 1 Drawing Sheet

U.S. PATENT DOCUMENTS

| | | | |
|---|---|---|---|
| 5,631,241 A | 5/1997 | Della Valle et al. |
| 5,644,049 A | 7/1997 | Giusti et al. |
| 5,662,913 A | 9/1997 | Capelli |
| 5,676,964 A | 10/1997 | Della Valle et al. |
| 5,693,065 A | 12/1997 | Rains, III |
| 5,709,546 A | 1/1998 | Waggoner |
| 5,716,981 A | 2/1998 | Hunter et al. |
| 5,739,176 A | 4/1998 | Dunn et al. |
| 5,763,410 A | 6/1998 | Edwardson et al. |
| 5,895,781 A | 4/1999 | Neumiller et al. |
| 5,925,334 A | 7/1999 | Rubin et al. |
| 5,968,542 A | 10/1999 | Tipton |
| 6,001,870 A | 12/1999 | Henkel |
| 6,013,657 A | 1/2000 | Lavon et al. |
| 6,063,061 A | 5/2000 | Wallace et al. |
| 6,071,305 A | 6/2000 | Brown et al. |
| 6,129,761 A | 10/2000 | Hubbell |
| 6,143,330 A | 11/2000 | Aaltonen et al. |
| 6,156,294 A | 12/2000 | Mautone |
| 6,156,792 A | 12/2000 | Hatton et al. |
| 6,203,822 B1 | 3/2001 | Schlesinger et al. |
| 6,224,857 B1 | 5/2001 | Romeo et al. |
| 6,248,371 B1 | 6/2001 | Domenico |
| 6,284,804 B1 | 9/2001 | Singh et al. |
| 6,342,251 B1 | 1/2002 | Illum et al. |
| 6,372,229 B1 | 4/2002 | Ollerenshaw et al. |
| 6,375,963 B1 | 4/2002 | Repka et al. |
| 6,395,295 B1 | 5/2002 | Hills et al. |
| 6,395,746 B1 | 5/2002 | Cagle et al. |
| 6,423,333 B1 | 7/2002 | Stedronsky et al. |
| 6,423,694 B1 | 7/2002 | Drutz et al. |
| 6,533,749 B1 | 3/2003 | Mitusina et al. |
| 6,541,116 B2 | 4/2003 | Michal et al. |
| 6,541,460 B2 | 4/2003 | Petito |
| 6,610,314 B2 | 8/2003 | Koenig et al. |
| 6,613,084 B2 | 9/2003 | Yang |
| 6,616,913 B1 | 9/2003 | Mautone |
| 6,623,513 B2 | 9/2003 | Biel |
| 6,623,521 B2 | 9/2003 | Steinke et al. |
| 6,632,457 B1 | 10/2003 | Sawhney |
| 6,676,930 B2 | 1/2004 | Mautone |
| 6,685,697 B1 | 2/2004 | Arenberg et al. |
| 6,686,346 B2 | 2/2004 | Nilsson et al. |
| 6,706,290 B1 | 3/2004 | Kajander et al. |
| 6,723,709 B1 | 4/2004 | Pressato et al. |
| 6,762,160 B2 | 7/2004 | Barbeau et al. |
| 6,770,729 B2 | 8/2004 | Van Antwerp |
| 6,812,196 B2 | 11/2004 | Rees et al. |
| 6,855,678 B2 * | 2/2005 | Whiteley ..................... 510/161 |
| 6,867,233 B2 | 3/2005 | Roselle et al. |
| 6,869,938 B1 | 3/2005 | Schwartz et al. |
| 6,891,037 B1 | 5/2005 | Hasler et al. |
| 6,919,348 B2 | 7/2005 | Wei |
| 6,936,579 B2 | 8/2005 | Urban |
| 6,953,772 B2 | 10/2005 | Lopes |
| 6,962,813 B2 | 11/2005 | Pier et al. |
| 6,989,195 B2 | 1/2006 | Anderson |
| 7,090,882 B2 | 8/2006 | Koefod et al. |
| 7,119,217 B2 | 10/2006 | Jiang et al. |
| 7,128,897 B2 | 10/2006 | Osbakken et al. |
| 7,220,431 B2 | 5/2007 | Sawchuk et al. |
| 7,238,363 B2 | 7/2007 | Mansouri et al. |
| 7,244,841 B2 | 7/2007 | Love et al. |
| 7,341,983 B2 | 3/2008 | Pedersen et al. |
| 7,410,480 B2 | 8/2008 | Muni et al. |
| 7,446,089 B2 | 11/2008 | Singh et al. |
| 7,494,963 B2 | 2/2009 | Ahmed et al. |
| 7,544,192 B2 | 6/2009 | Eaton et al. |
| 7,714,011 B2 | 5/2010 | Clarot et al. |
| 2001/0044651 A1 | 11/2001 | Steinke et al. |
| 2001/0051613 A1 | 12/2001 | Illum et al. |
| 2002/0022588 A1 | 2/2002 | Wilkie et al. |
| 2002/0029015 A1 | 3/2002 | Camenzind et al. |
| 2002/0055158 A1 | 5/2002 | Greene et al. |
| 2002/0062147 A1 | 5/2002 | Yang |
| 2002/0187918 A1 | 12/2002 | Urban |
| 2003/0009213 A1 | 1/2003 | Yang |
| 2003/0079758 A1 | 5/2003 | Siegel et al. |
| 2003/0133883 A1 | 7/2003 | Finnegan et al. |
| 2003/0139382 A1 | 7/2003 | Wall et al. |
| 2003/0157687 A1 | 8/2003 | Greene et al. |
| 2003/0199969 A1 | 10/2003 | Steinke et al. |
| 2003/0235602 A1 | 12/2003 | Schwarz |
| 2004/0101506 A1 * | 5/2004 | Fust ......................... 424/70.31 |
| 2004/0106987 A1 | 6/2004 | Palasis et al. |
| 2004/0110738 A1 | 6/2004 | Gillis et al. |
| 2004/0116958 A1 | 6/2004 | Gopferich et al. |
| 2004/0117006 A1 | 6/2004 | Lewis et al. |
| 2004/0143001 A1 | 7/2004 | Love et al. |
| 2004/0204399 A1 | 10/2004 | Osbakken et al. |
| 2004/0213758 A1 | 10/2004 | Sefton et al. |
| 2004/0214753 A1 | 10/2004 | Britten et al. |
| 2005/0003007 A1 | 1/2005 | Boix et al. |
| 2005/0032668 A1 | 2/2005 | Pedersen et al. |
| 2005/0042240 A1 | 2/2005 | Utterberg et al. |
| 2005/0043706 A1 | 2/2005 | Eaton et al. |
| 2005/0064508 A1 | 3/2005 | Belcher et al. |
| 2005/0080396 A1 | 4/2005 | Rontal |
| 2005/0106728 A1 | 5/2005 | Burgess et al. |
| 2005/0147679 A1 | 7/2005 | Petito et al. |
| 2005/0220895 A1 | 10/2005 | Bucalo et al. |
| 2005/0226937 A1 | 10/2005 | O'Hagan et al. |
| 2005/0244339 A1 | 11/2005 | Jauernig et al. |
| 2005/0282722 A1 | 12/2005 | McReynolds et al. |
| 2006/0003008 A1 | 1/2006 | Gibson et al. |
| 2006/0018945 A1 | 1/2006 | Britigan et al. |
| 2006/0035808 A1 | 2/2006 | Ahmed et al. |
| 2006/0045850 A1 * | 3/2006 | Namburi et al. ................ 424/46 |
| 2006/0051385 A1 | 3/2006 | Scholz |
| 2006/0106361 A1 | 5/2006 | Muni et al. |
| 2006/0205621 A1 | 9/2006 | Borazjani et al. |
| 2006/0210605 A1 | 9/2006 | Chang et al. |
| 2007/0207192 A1 | 9/2007 | Holl et al. |
| 2007/0264310 A1 | 11/2007 | Hissong et al. |
| 2007/0264342 A1 | 11/2007 | Oliver et al. |
| 2007/0264353 A1 | 11/2007 | Myntti et al. |
| 2008/0010947 A1 | 1/2008 | Huang et al. |
| 2008/0248558 A1 | 10/2008 | Deinhammer et al. |
| 2009/0005339 A1 * | 1/2009 | Scholz et al. ................. 514/53 |
| 2010/0240770 A1 | 9/2010 | Qi et al. |

FOREIGN PATENT DOCUMENTS

| | | | |
|---|---|---|---|
| EP | 1 374 856 A1 | 1/2004 |
| FR | 2 710 529 A1 | 4/1995 |
| JP | 52-007428 | 1/1977 |
| RU | 222 8203 | 5/2004 |
| SU | 1128917 A1 | 12/1984 |
| SU | 1699430 A1 | 12/1991 |
| WO | WO 94/05330 | 3/1994 |
| WO | WO 95/03036 | 2/1995 |
| WO | WO 97/38698 | 10/1997 |
| WO | WO 98/09622 * | 3/1998 |
| WO | WO 99/27905 A | 6/1999 |
| WO | WO 00/56283 | 9/2000 |
| WO | WO 03/061579 A2 | 7/2003 |
| WO | WO 03/092745 A1 | 11/2003 |
| WO | WO 2004/009143 A1 | 1/2004 |
| WO | WO 2004/024187 A2 | 3/2004 |
| WO | WO 2005/000029 A2 | 1/2005 |
| WO | WO 2005/089670 A1 | 9/2005 |
| WO | WO 2006/099386 A2 | 9/2006 |
| WO | WO 2008/097317 A1 | 8/2008 |

OTHER PUBLICATIONS

Ehrlich et al., "Mucosal Biofilm Formation on Middle-Ear Mucosa in the Chinchilla Model of Otitis Media", JAMA 287(13):1710-15 (2002).

Fergie, N. et al., "Is otitis media with effusion a biofilm infection?", Clin Otolaryngol Allied Sci. 29(1):38-46 (2004).

Ferguson B.J. and Stolz D.B., "Demonstration of biofilm in human bacterial chronic rhinosinusitis", Am J Rhinol 19:452-457, 2005.

Ramadan H.H., Sanclement J.A. and Thomas J.G., "Chronic rhinosinusitis and biofilms", Otolaryngol Head Neck Surg. 132:414-417, 2005.

Benninger M.S., Ferguson B.J., Hadley J.A., et al., "Adult chronic rhinosinusitis: Definitions, diagnosis, epidemiology, and pathophysiology", Otolaryngol Head Neck Surg 129 (3 suppl):S1-S32, 2003.

Nadel D.M., Lanza D.C., and Kennedy D.W., "Endoscopically guided cultures in chronic sinusitis", Am J Rhinol 12:233-241, 1998.

Stepanovic S, Vukovic D, Dakic I, et al., "A modified microtiter-plate test for quantification of staphylococcal biofilm formation", J Microbiol Methods 40:175-179, 2000.

Gotz F., "Staphylococcus and biofilms", Mol Microbiol 43:1367-1378, 2002.

Lethbridge-çejku M, Rose D, Vickerie J. Summary health statistics for US adults: National Health Interview Survey, 2004. National Center for Health Statistics. Vital Health Stat 2006;10 (228). Available: http://www.cdc.gov/nchs/fastats/sinuses.htm.

Rosiak, J.M. et al., "Radiation Formation of Hydrogels for Biomedical Purposes. Some Remarks And Comments", Radiat. Phys. Chem. vol. 46, No. 2, pp. 161-168, 1995.

Costerton J.W., Stewart P.S. and Greenberg E.P., "Bacterial biofilms: A common cause of persistent infections", Science 284:1318-1322, 1999.

Morris D.P. and Hagr A., "Biofilm: Why the sudden interest?" J Otolaryngol 34(suppl 2):S56-S5, 2005.

Hall-Stoodley L, Hu F.Z., Gieseke A, et al., "Direct detection of bacterial biofilms on the middle-ear mucosa of children with chronic otitis media." JAMA 296:202-211, 2006.

Sanderson A.R., Leid J.G., and Hunsaker D., "Bacterial biofilms on the sinus mucosa of human subjects with chronic rhinosinusitis", Laryngoscope 116:1121-1126 (2006).

Sanclement J.A., Webster P., Thomas J., and Ramadan H.H., "Bacterial biofilms in surgical specimens of patients with chronic rhinosinusitis", Laryngoscope 115:578-582, 2005.

Bendouah Z., Barbeau J., Hamad W.A., and Desrosiers M., "Biofilm formation by Staphylococcus aureus and Pseudomonas aeruginosa is associated with an unfavorable evolution after surgery for chronic sinusitis and nasal polyposis", Otolaryngol Head Neck Surg. 134:991-996, 2006.

Bhattacharyya N., and Kepnes L.J., "The microbiology of recurrent rhinosinusitis after endoscopic sinus surgery", Arch Otolaryngol Head Neck Surg. 125:1117-1120, 1999.

Cryer J., Schipor I., Perloff J.R., and Palmer J.N., "Evidence of bacterial biofilms in human chronic sinusitis", ORL J Otorhinolaryngol Relat Spec 66:155-158, 2004.

Meltzer E.O., Hamilos D.L., Hadley J.A., et al., "Rhinosinusitis: Establishing definitions for clinical research and patient care", J Allergy Clin Immunol 114(suppl):S155-S212, 2004.

Chiu A.G., and Kennedy D.W., "Surgical management of chronic rhinosinusitis and nasal polyposis: a review of the evidence", Curr Allergy Asthma Rep 4:486-489, 2004.

Bhattacharyya N., "Clinical outcomes after endoscopic sinus surgery", Curr Opin Allergy Clin Immunol 6:167-171, 2006.

Wormald P.J., Psaltis A., and Ha K., "A sheep model for the study of biofilms in sinusitis", In Programs and abstracts of the 52nd Annual Meeting of the American Rhinologic Society, Toronto, Ontario, Canada, Sep. 16, 2006.

Anglen J.O., Apostoles S., Christensen G., and Gainor B., "The efficacy of various irrigation solutions in removing slime-producing Staphylococcus", J Orthop Trauma 8:390-396, 1994.

Chole, Richard A. and Faddis, Brian T., Evidence for Microbial Biofilms in Cholesteatomas, Arch Otolaryngol Head and Neck Surg. 2002; 128: 1129-1133. Downloaded Apr. 17, 2007 from Medtronic Xomed at www.archoto.com.

Desrosiers M. Refractory chronic rhinosinusitis: pathophysiology and management of chronic rhinosinusitis persisting after endoscopic sinus surgery. Curr Allergy Asthma Rep 2004;4:200-7.

Smith TL, Batra PS, Seiden AM, Hannley M. Evidence supporting endoscopic sinus surgery in the management of adult chronic sinusitis: a systematic review. Am J Rhinol 2005;19:537-43.

Perloff JR, Palmer JN. Evidence of bacterial biofilms on frontal recess stents in patients with chronic rhinosinusitis. Am J Rhinol 2004;18:377-80.

Wright ED, Frenkiel S. Infectious adult rhinosinusitis: etiology, diagnosis, and management principles. J Otolaryngol 2005;34(suppl 1):S7-13.

Luong A, Marple BF. Sinus surgery: indications and techniques. Clin Rev Allergy Immunol 2006;30:217-22. Abdi-Ali A, Mohammadi-Mehr M, Agha Alaei Y. Bactericidal activity of various antibiotics against biofilm-producing Pseudomonas aeruginosa. Int J Antimicrob Agents 2206;27:196-200.

Jefferson KK, Goldmann DA, Pier GB. Use of confocal microscopy to analyze the rate of vancomycin penetration through Staphylococcus aureus biofilms. Antimicrob Agents Chemother 2005;49:2467-73.

Walters MC 3rd, Roe F, Bugnicourt A, Franklin MJ, Stewart PS. Contributions of antibiotic penetration, oxygen limitation, and low metabolic activity to tolerance of Pseudomonas aeruginosa biofilms to ciprofloxacin and tobramycin. Antimicrob Agents Chemother 2003;47:317-23.

Palmer JN. Bacterial biofilms: do they play a role in chronic sinusitis? Otolaryngol Clin N Am 2005;38:1193-1201.

Donlan RM. Biofilms: microbial life on surfaces. Emerg Infect Dis 2002;8:881-90.

Potera C. Forging a link between biofilms and disease. Science 1999;283:1837, 1839.

Post JC, Stoodley P, Hall-Stoodley L, Ehrlich GD. The role of biofilms in otolaryngologic infections. Curr Opin Otolaryngol Head Neck Surg 2004;12:185-90.

Tonnaer EL, Graamans K, Sanders EA, Curfs JH. Advances in understanding the pathogenesis of Pneumococcal otitis media. Pediatr Infect Dis J 2006;25:546-52.

Rayner MG, Zhang Y, Gorry MC, Chen Y, Post CJ, Ehrlich GD. Evidence of bacterial metabolic activity in culture-negative otitis media with effusion. JAMA 1998;279:296-9.

Dingman JR, Rayner MG, Mishra S, Zhang Y, Ehrlich MD, Post JC, et al. Correlation between presence of viable bacteria and presence of endotoxin in middle-ear effusions. J Clin Microbiol 1998;36:3417-9.

Perloff JR, Palmer JN. Evidence of bacterial biofilms in a rabbit model of sinusitis. Am J Rhinol 2005;19:1-9.

Chiu A, Antunes M, Feldman M, Cohen N. Dose-dependent effects of topical tobramycin in an animal model of Pseudomonas sinusitis. In: Programs and abstracts of the 52nd Annual Meeting of the American Rhinologic Society; Sep. 16, 2006; Toronto, ON, Canada.

Witterick IJ, Kolenda J. Surgical management of chronic rhinosinusitis Immunol Allergy Clin N Am 2004;24:119-34.

Lieu JE, Piccirillo JF. Methodologic assessment of studies on endoscopic sinus surgery. Arch Otolaryngol Head Neck Surg 2003;129:1230-5.

Lavigne F, Tulic MK, Gagnon J, Hamid Q. Selective irrigation of the sinuses in the management of chronic rhinosinusitis refractory to medical therapy: a promising start. J Otolaryngol 2004;33:10-16.

Stoeckli, Sandro J. et al., "A Prospective Randomized Double-Blind Trial of Fibrin Glue for Pain and Bleeding After Tonsillectomy", Laryngoscope 109: pp. 652-655, (Apr. 1999).

Granick Mark M.D. et al., "Toward a common language: surgical wound bed preparation and debridement", Wound Repair and Regeneration, 14, S1-S10, © the Wound Healing Society, (2006).

Stetter, Christopher et al., "Skin grafting of a chronic leg ulcer with combined Versajet™ —V.A.C. therapy", XP-002566870 Case Reports, JDDG, 4:739-742 (2006).

Nagoba, B.S. et al., A Simple and Effective Approach for the Treatment of Chronic Wound Infections Caused by Multiple Antibiotic Resistant Escherichia coli, Journal of Hospital Infection, 69:177-180 (2008).

Banin, Ehud et al., "Chelator-Induced Dispersal and Killing of Pseudomonas aeruginosa Cells in a Biofilm", Applied and Environmental Microbiology, vol. 72, No. 3, pp. 2064-2069 (Mar. 2006).

Chang, D.M., the Binding of Free Calcium Ions in Aqueous Solution Using Chelating Agents, Phosphates and Poly (Acrylic Acid), JAOCS, vol. 60, No. 3, pp. 618-622 (Mar. 1983).

"Medicine Encyclopedia" M., RLS, p. 561( 2001)—Miramistin solution 0.01%.

Yamada et al., "Chitosan Based Water-Resistant Adhesive. Analogy to Mussel Glue", Biomacromolecules 2000, 1 (2), pp. 252-258 (Apr. 13, 2000).

"Protein Polymer Technologies Product Research" dated Mar. 28, 2006, 2 pages, downloaded from the Internet Archive at: http://web.archive.org/web/20060328113942/www.ppti.com/Market/Research.html.

Gross, Charles W., et al., "Autologus Fibrin Sealant Reduces Pain After Tonsillectomy", Tthe Laryngoscope 111, pp. 259-263 (Feb. 2001).

Kitajiri et al., "Relief of Post-Tonsillectomy Pain by Release of Lidocaine From Fibrin Glue", The Laryngoscope 111, pp. 642-644 (Apr. 2001).

Vaiman Michael et al., "Fibrin Sealant Reduces Pain After Tonsillectomy: Prospective Randomized Study", Annals of Otology, Rhinology & Laryngology 115 (7), pp. 483-489 (2006).

Archer, Sanford M. MD, *Nasal Polyps, Nonsurgical Treatment*, eMedicine, dated Oct. 19, 2004, downloaded from the Internet Archive at: http://web.archive.org/web/20041019082359/http://www.emedicine.com/ent/topic334.htm.

Atridox®, Package insert and Carton Label Rev 7 (Feb. 2003).

Kumar et al., "Inhibition of Inflammation and Roflumilast and Dexamethasone in Murine Chronic Asthma", Journal of Pharmacology and Experimental Therapeutics, vol. 307, No. 1, pp. 349-355 (2003).

CollaGenex Atridox® web page, dated Sep. 26, 2004, downloaded from the Internet Archive at: http://web.archive.org/web/20041205004132/collagenex.com/pr_atridox.asp.

Lechapt-Zalcman et al., *Increased expression of matrix metalloproteinase-9 in nasal polyps*, Journal of Pathology, 193:233-241 (2001).

Kyung, Lee S. et al., *Doxycycline reduces airway inflammation and hyperresponsiveness in a murine model of toluene diisocyanate-induced asthma*, Journal of Allergy and Clinical Immunology [online] (May 2004).

Watelet, J.B. et al., *Matrix metalloproteinases MMP-7, MMP-9 and their tissue inhibitor TIMP-1: expression in chronic sinusitis vs. nasal polyposis*, Allergy, 59:54-60 (2004).

Plateltex, "Reduce fibrosis-Reducing scarring-Autologous Platelets", accessed on Jan. 26, 2010 from: http://www.plateltex.com/lp_reduce_fibosis.html.

* cited by examiner

EXTRACELLULAR POLYSACCHARIDE SOLVATING SYSTEM FOR TREATMENT OF BACTERIAL EAR CONDITIONS

CROSS REFERENCE TO RELATED APPLICATION

This application is a continuation-in-part of U.S. patent application Ser. No. 11/431,495 filed May 10, 2006, now abandoned, the entire disclosure of which is incorporated herein by reference.

FIELD OF THE INVENTION

This invention relates to the treatment of chronic otitis media and other bacterial ear conditions.

BACKGROUND

Biofilm formation may be a factor in the pathogenesis of chronic otitis media with effusion, see Post, J. C., "Direct evidence of bacterial biofilms in otitis media", Laryngoscope 111(12):2083-94 (2001), Ehrlich et al., "Mucosal Biofilm Formation on Middle-Ear Mucosa in the Chinchilla Model of Otitis Media", JAMA 287(13):1710-15 (2002) and Fergie, N et al., "Is otitis media with effusion a biofilm infection?", Clin Otolaryngol Allied Sci. 29(1):38-46 (2004). Biofilms form when bacteria interact with a surface to form polymeric films (sometimes referred to as exopolysaccharide or extracellular polysaccharide polymers) that coat the surface and provide a living colony for further bacterial proliferation. Bacteria lodged in biofilms are much more difficult to remove or kill than bacteria in a plaktonic (suspended) state, and are extremely resistant to many antibiotics and biocides.

SUMMARY OF THE INVENTION

Saline solutions and antibiotics may be applied to bacterial biofilms in the middle ear but in difficult cases may not provide adequate relief from chronic otitis media. Various techniques and products have been employed to remove or kill bacteria in biofilms found in dental water lines and on medical instruments or other extracorporeal surfaces, but may be poorly suited for treating the delicate surfaces and fragile structures in the middle and inner ear. It would be desirable to remove or kill bacteria inhabiting a biofilm within the middle or inner ear, and if possible to remove or disrupt the biofilm itself sufficiently to discourage bacterial recolonization and biofilm reformation. It would also be desirable to do so while meeting biocompatibility requirements for contact with human tissue, and while using small dosages of administered materials and short periods of application. It has now been discovered that a solvating system comprising a metal ion sequestering agent and surfactant is surprisingly effective in disrupting bacterial biofilms within the middle or inner ear while being gentle enough for application directly into this delicate and sensitive area.

The invention provides in one aspect a method for treating chronic otitis media and other bacterial ear conditions, which method comprises:

a) applying a solvating system comprising a metal ion sequestering agent and greater than 0.2 wt. % surfactant to a bacterial biofilm attached or adhered to at least a portion of the middle or inner ear, and b) detaching, removing or otherwise disrupting at least a part of the biofilm.

The invention provides in another aspect a method for treating chronic otitis media and other bacterial ear conditions, which method comprises:

a) applying a solvating system comprising a metal ion sequestering agent, a zwitterionic surfactant, and sufficient buffer so that the solvating system has a pH greater than 5 to a bacterial biofilm attached or adhered to at least a portion of the middle or inner ear, and b) detaching, removing or otherwise disrupting at least a part of the biofilm.

The invention provides in yet another aspect a solvating system for disrupting bacterial biofilms on tissue, the composition comprising a metal ion sequestering agent, greater than 0.2 wt. % surfactant, and an antimicrobial agent.

The invention provides in another aspect a solvating system for disrupting bacterial biofilms on tissue, the composition comprising a metal ion sequestering agent, a zwitterionic surfactant, and sufficient buffer so that the solvating system has a pH greater than 5.

The disclosed solvating systems may be used to treat chronic otitis media (e.g., otitis media with effusion and recurrent otitis media), cholesteatoma and other bacterial ear conditions. The solvating systems may also be used to treat sinusitis (e.g., chronic rhinosinusitis) and other bacterial sinus conditions.

BRIEF DESCRIPTION OF THE DRAWING

Like reference symbols in the various figures of the drawing indicate like elements. The elements in the drawing are not to scale.

DETAILED DESCRIPTION OF THE PREFERRED EMBODIMENTS

The following detailed description describes certain embodiments and is not to be taken in a limiting sense. All weights, amounts and ratios herein are by weight, unless otherwise specifically noted. The terms shown below have the following meanings:

The term "antimicrobial agent" refers to a substance having the ability to cause greater than a 90% numeric reduction (viz., greater than a 1-log order reduction) in a population of one or more of *Staphylococcus aureus, Pseudomonas aeruginosa, Streptococcus pneumonia, Haemophilus influenzae* or *Moraxella catarrhalis* or any other bacteria implicated in the etiology of COME, RAOM or cholesteatoma using the bacterial plate count procedure described below in the Examples.

The terms "attached" and "adhered" when used in reference to a bacterial biofilm and a surface mean that the biofilm is established on and at least partially coats or covers the surface, and has some resistance to removal from the surface. As the nature of this relationship is complex and poorly understood, no particular mechanism of attachment or adherence is intended by such usage.

The term "bacterial biofilm" means a community of bacteria attached to a surface, with the organisms in the community being contained within an extracellular polymeric substance (EPS) matrix produced by the bacteria.

The term "biocompatible" when used in reference to a substance means that the substance presents no significant deleterious or untoward effects upon the body.

The term "biodegradable" when used in reference to a substance means that the substance will degrade or erode in vivo to form smaller chemical species. Such degradation process may be enzymatic, chemical or physical.

The term "bioresorbable" when used in reference to a substance means that the substance is capable of being absorbed by the body.

The terms "detaching", "removing" and "disrupting" when used in reference to a bacterial biofilm attached or adhered to a surface mean that at least a significant amount of the biofilm initially present on the surface no longer is attached or adhered to the surface. No particular mechanism of detachment, removal or disruption is intended by such usage.

The term "sequestering agent" means a chemical that will combine with another material, especially a metal ion, to discourage or prevent the material from coming out of solution. The term "metal ion sequestering agent" means a sequestering agent that will combine with one or more metal ions such as alkali metals, alkaline earth metals, iron and the like to discourage or prevent the metal ion from coming out of solution. In order of increasing atomic number the alkali metals are lithium, sodium, potassium, rubidium, cesium, and francium, and the alkaline earth metals are beryllium, magnesium, calcium, strontium, barium, and radium.

The term "solvating" means to form a solution or dispersion containing a solvent or other carrier within which a solute is dissolved or suspended.

Figure 1:
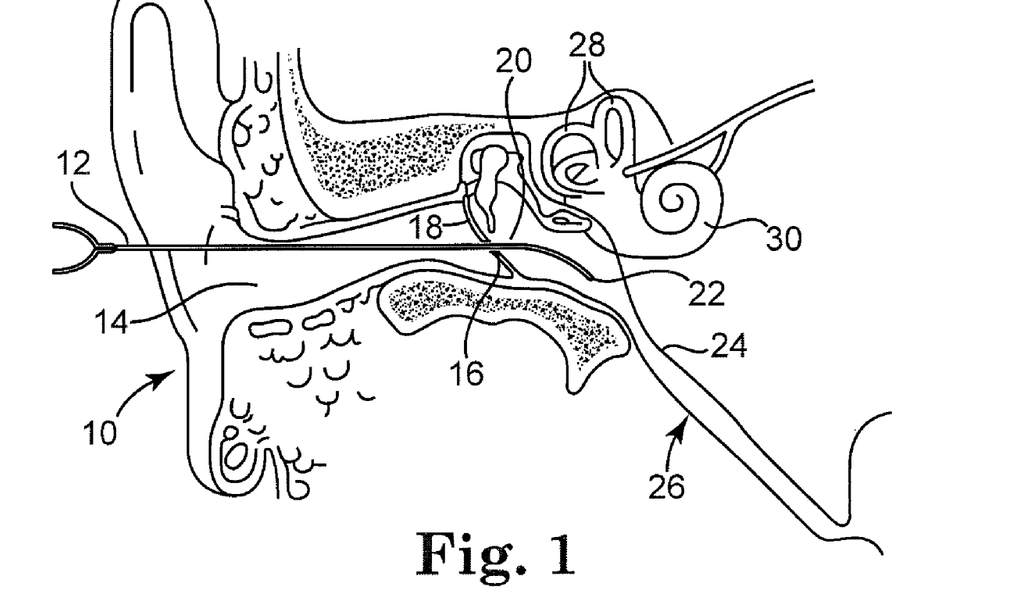
FIG. 1 is a schematic cross-sectional view of a middle ear undergoing treatment via the disclosed method.

Referring to FIG. 1, one method for applying the solvating system within ear 10 may be performed by inserting cannula 12 through ear canal 14 and ear tube 16 (which may for example be placed via myringotomy) in tympanic membrane 18 and thence into middle ear 20. Cannula 12 may also be inserted in other ways without myringotomy, such as through a needle or other guidance device directed through the ear, Eustachian tubes or nose, and operated blindly or by using guided techniques such as microendoscopy, virtual image guided endoscopy, or image guided surgery using a flexible, tip tracked device. As shown in FIG. 1, the distal end 22 of cannula 12 is positioned above isthmus 24 of Eustachian tube 26. Cannula 12 may be positioned and if need be modified in shape or size so as to treat other portions of middle ear 20 (which for purposes of this discussion will be deemed to include at least the tympanic membrane, the lining of the middle ear, interior structures such as the ossicular chain and bordering structures such as the mastoid) or to treat portions of the inner ear (which for purposes of this discussion will be deemed to include at least semicircular canals 28 and cochlea 30). For example, if treatment in the inner ear is desired, a further access opening (e.g., in a membrane near the round window or oval window) may be made.

Figure 2:
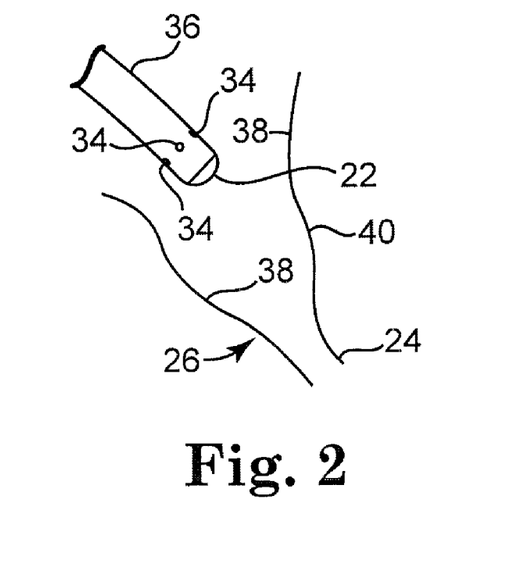
FIG. 2 is an enlarged view of a portion of FIG. 1 showing application of the disclosed solvating system to a bacterial biofilm proximate the Eustachian tube isthmus.

FIG. 2 shows an enlarged view of a portion of FIG. 1. The solvating system may be dispensed through orifices 34 located in sidewall 36, and dripped, sprayed or otherwise administered onto a bacterial biofilm such as biofilm 38 disposed on upper portion 40 of Eustachian tube 26.

The solvating system can be used to break down bacterial biofilms located in the middle or inner ear and consequently aid in their detachment, removal or disruption. The solvating system is biocompatible with the delicate tissues and structures of the middle or inner ear, and desirably does not contain ingredients which might potentially harm such tissues or structures or unduly compromise long-term hearing. The solvating system desirably has a sufficiently low viscosity to enable easy delivery to the bacterial biofilm using for example power spray or other spray application, lavage, misting, mopping, wicking or dripping. The solvating system desirably also may be easily removed from the treatment site by subsequent flushing, rinsing, draining or absorption. While not wishing to be bound by theory, the metal ion sequestering agent may complex, bind or otherwise tie up metal ions which may crosslink, bridge or otherwise assist in binding together the polymer chains in an exopolysaccharide or extracellular polysaccharide matrix. The solvating agent may then surround the unbound polymer chains or fragments, breaking down the matrix, solvating the unbound polymer chains or fragments, and bringing them into solution or suspension where they can be easily flushed or otherwise removed from the treated middle ear or inner ear tissues or structures using for example additional amounts of the solvating system or a separate rinsing agent.

The metal ion sequestering agent desirably is a mild acid whose acidity is sufficient to sequester one or more metal ions in the exopolysaccharide or extracellular polysaccharide matrix, but which is not so acidic so as to harm the treated middle or inner ear tissue. Metal ions of particular interest (due to their likely involvement in the targeted bacterial biofilms) include sodium, calcium and iron. The metal ion sequestering agent desirably is water-soluble, nontoxic and not prone to aggravate long-term hearing loss. Representative acids include but are not limited to carboxylic acids, diacids, or triacids such as formic acid, acetic acid, chloroacetic acid, dichloroacetic acid, oxalic acid, oxamic acid, glycolic acid, lactic acid, pyruvic acid, aspartic acid, fumaric acid, maleic acid, succinic acid, iminodiacetic acid, glutaric acid, 2-ketoglutaric acid, glutamic acid, adipic acid, citric acid, glucuronic acid, mucic acid, nitrilotriacetic acid, salicylic acid, ketopimelic acid, benzoic acid, mandelic acid, chloromandelic acid, phenylactic acid, phthalic acid and boric acid; mineral acids such as hydrochloric acid, orthophosphoric acid and phosphonic acid; and mixtures thereof. Citric acid is a preferred acid. The metal ion sequestering agent may for example be present at a concentration of at least about 0.01 M, at least about 0.05 M or at least about 0.1 M, e.g., about 0.01 to about 0.5 M, about 0.05 to about 0.4 M or about 0.1 to about 0.3 M. Increased metal ion sequestering agent amounts may promote faster biofilm breakup.

The solvating system also includes a surfactant. The surfactant desirably is water-soluble and nontoxic. Exemplary surfactants include anionic surfactants, nonionic surfactants, cationic surfactants and zwitterionic surfactants. Exemplary anionic surfactants include but are not limited to $C_6$-$C_{24}$ alkylbenzene sulfonates; $C_6$-$C_{24}$ olefin sulfonates; $C_6$-$C_{24}$ paraffin sulfonates; cumene sulfonate; xylene sulfonate; $C_6$-$C_{24}$ alkyl naphthalene sulfonates; $C_6$-$C_{24}$ alkyl or dialkyl diphenyl ether sulfonates or disulfonates, $C_4$-$C_{24}$ mono or dialkyl sulfosuccinates; sulfonated or sulfated fatty acids; $C_6$-$C_{24}$ alcohol sulfates (for example $C_6$-$C_{12}$ alcohol sulfates); $C_6$-$C_{24}$ alcohol ether sulfates having 1 to about 20 ethylene oxide groups; $C_4$-$C_{24}$ alkyl, aryl or alkaryl phosphate esters or their alkoxylated analogues having 1 to about 40 ethylene, propylene or butylene oxide units; and mixtures thereof. For example, the anionic surfactant may be sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate (also known as sodium lauryl sulfate) or sodium glycodeoxycholate.

Exemplary cationic surfactants include but are not limited to quaternary amine compounds having the formula:

where R, R', R" and R'" are each a $C_1$-$C_{24}$ alkyl, aryl or aralkyl group that can optionally contain one or more P, O, S or N heteroatoms, and X is F, Cl, Br, I or an alkyl sulfate. For example, the cationic surfactant may be hexadecylpyridinium chloride monohydrate or hexadecyltrimethylammonium bromide.

Exemplary nonionic surfactants include but are not limited to $C_6$-$C_{24}$ alcohol ethoxylates (for example $C_6$-$C_{14}$ alcohol ethoxylates) having 1 to about 20 ethylene oxide groups (for example about 9 to about 20 ethylene oxide groups); $C_6$-$C_{24}$ alkylphenol ethoxylates (for example $C_8$-$C_{10}$ alkylphenol ethoxylates) having 1 to about 100 ethylene oxide groups (for example about 12 to about 20 ethylene oxide groups); $C_6$-$C_{24}$ alkylpolyglycosides (for example $C_6$-$C_{20}$ alkylpolyglycosides) having 1 to about 20 glycoside groups (for example about 9 to about 20 glycoside groups); $C_6$-$C_{24}$ fatty acid ester ethoxylates, propoxylates or glycerides; C4-$C_{24}$ mono or di alkanolamides; and mixtures thereof. For example, the nonionic surfactant may be polyoxyethyleneglycol dodecyl ether, N-decanoyl-N-methylglucamine, digitonin, n-dodecyl B-D-maltoside, octyl B-D-glucopyranoside, octylphenol ethoxylate, polyoxyethylene (8) isooctyl phenyl ether, polyoxyethylene sorbitan monolaurate or polyoxyethylene (20) sorbitan monooleate.

Exemplary zwitterionic surfactants include but are not limited to aminoalkylsulfonate compounds having the formula:

where R, R', R" and R'" are each a $C_1$-$C_{24}$ alkyl, aryl or aralkyl group that can optionally contain one or more P, O, S or N heteroatoms; amine oxide compounds having the formula:

where R, R' and R" are each a $C_1$-$C_{24}$ alkyl, aryl or aralkyl group that can optionally contain one or more P, O, S or N heteroatoms; and betaine compounds having the formula:

where R, R' and R" are each a $C_1$-$C_{24}$ alkyl, aryl or aralkyl group that can optionally contain one or more P, O, S or N heteroatoms, and n is about 1 to about 10. For example, the zwitterionic surfactant may be 3-[(3-cholamidopropyl)dimethylammonio]-2-hydroxy-1-propane sulfonate, 3-[(3-cholamidopropyl)dimethylammonio]-1-propane sulfonate (sometimes referred to as CHAPS), 3-(decyldimethylammonio)propanesulfonate inner salt (sometimes referred to as caprylyl sulfobetaine), or N-dodecyl-N,N-dimethyl-3-ammonio-1-propanesulfonate.

Preferred surfactants include alkyl sulfates, alkyl sulfonates, aryl sulfonates and zwitterionic surfactants. The desired surfactants may be obtained as pure compounds or in some instances may be obtained by using products such as liquid Castile soap. The surfactant may for example be present at a concentration of at least about 0.002 M, at least about 0.005 M or at least about 0.01 M, e.g., about 0.002 to about 1 M, about 0.005 to about 0.7 M or about 0.01 to about 0.5 M. Expressed on a weight basis, the surfactant preferably is greater than 0.2 wt. % of the solvating system and may for example be about 0.3% to about 30%, about 0.5% to about 25% or about 1% to about 20% of the solvating system. Increased surfactant amounts may promote faster biofilm breakup.

The solvating system may optionally include a variety of other ingredients, including water and other solvents (e.g., alcohols), buffering agents, antimicrobial agents and a variety of adjuvants. Preferably the solvating system contains water and one or more buffering agents. The buffering agent preferably maintains the solvating system at an appropriate pH for contacting human tissue, and desirably at a pH greater than 5. For example, the solvating system may be buffered to have a near-neutral pH, e.g., a pH greater than 5 and less than 8.5. Buffering agents may for example be up to about 25% of the solvating system. Exemplary buffering agents include but are not limited to potassium chloride, glycine, potassium hydrogen phthalate, sodium acetate, potassium hydrogen phthalate, barbitone sodium and sodium citrate. When the metal ion sequestering agent is a mild acid, the buffering agent desirably is a salt of that acid.

Solvating systems containing one or more antimicrobial agents are also preferred. The EPS matrix allows the biofilm to stick to an underlying surface and also protects the embedded organisms; thus, bacteria in biofilms are approximately 100 to 1000 times more resistant to the effects of antibiotics than planktonic bacteria. After the biofilm has been broken down into unbound polymers or fragments and solvated or otherwise disrupted by the solvating system, an antimicrobial agent can much more effectively attack the remaining bacteria. Exemplary antimicrobial agents include active oxygen compounds such as hydrogen peroxide, isolated or equilibrium derived or isolated peracids such as chloroperbenzoic acids, peracetic acid, perheptanoic acid, peroctanoic acid, perdecanoic acid, per formic acid, percitric acid, perglycolic acid, perlactic acid, perbenzoic acid, and monoester peracids derived from diacids or diesters such as adipic, succinic, glutaric, or malonic acid; amphenicols; ampicillins; ansamycins; beta-lactams such as carbacephems, carbapenems, cephalosporins, cephamycins, monobactams, oxacephems, penicillins and any of their derivatives; carboxylic esters such as p-hydroxy alkyl benzoates and alkyl cinnamates; chitosan salts; cubic-phase lipids; gallium-containing antimicrobial agents such as gallium acetylacetonate, gallium bromide, gallium chloride, gallium fluoride, gallium iodide, gallium maltolate, gallium nitrate, gallium nitride, gallium percolate, gallium phosphide and gallium sulfate; iodo-compounds and other active halogen compounds such as iodine, interhalides, polyhalides, metal hypochlorites, hypochlorous acid, metal hypobromites, hypobromous acid, chloro- and bromo-hydantoins, chlorine dioxide and sodium chlorite; lincosamides; macrolides; nitrofurans; organic peroxides including benzoyl peroxide and alkyl benzoyl peroxides; ozone; phenolic derivatives including o-phenyl phenol, o-benzyl-p-chlorophenol, tert-amyl phenol and $C_1$-$C_6$ alkyl hydroxy benzoates; quaternary ammonium compounds such as alkyldimethylbenzyl ammonium chloride and dialkyldimethyl ammonium chloride; quinolines; singlet oxygen generators; sulfonamides; sulfones; sulfonic acids such as dodecylbenzene sulfonic acid; tetracyclines; vancomycin; derivatives thereof and mixtures thereof. Many of these recited agents represent classes containing useful specific materials whose individual utility will be recognized by persons having ordinary skill in the art. For example, exemplary penicillins include but are not limited to amdinocillin, amdinocillin pivoxil, amoxicillin ampicillin, apalcillin, aspoxicillin, axidocillin, azlocillin, acampicillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G. procaine, penicillin N, penicillin O, penicillin V, penicillin V banzathine, penicillin V hydrabamine, penimepicycline, phenethicillin potassium, piperacillin, pivampicillin propicillin, quinacillin, sulbenicillin, sultamicillin, talampicillin, temocillin, ticarcillin and mixtures thereof or with other materials (e.g., penicillins combined with clavulanic aid such as the combination of amoxicillin and clavulanic acid available as AUGMENTIN™ from GlaxoSmithKline).

Preferably the antimicrobial agent provides greater than a 99% numeric reduction (viz., at least a 2-log order reduction), greater than a 99.9% numeric reduction (viz., at least a 3-log order reduction), greater than a 99.99% numeric reduction (viz., at least a 4-log order reduction) or greater than a 99.999% numeric reduction (viz., at least a 5-log order reduction) in a population of one or more of *S. aureus, P. aeruginosa, S. pneumonia, H. influenzae* or *M. catarrhalis* bacteria using the bacterial plate count procedure described below in the Examples.

The solvating system may contain additional therapeutic agents. Exemplary therapeutic agents include any material suitable for otologic use including analgesics, anti-cholinergics, anti-fungal agents, antihistamines, steroidal or non-steroidal anti-inflammatory agents, anti-parasitic agents, antiviral agents, biostatic compositions, chemotherapeutic/antineoplastic agents, cytokines, decongestants, immunosuppressors, mucolytics, nucleic acids, peptides, proteins, steroids, vasoconstrictors, vitamins, mixtures thereof, and other therapeutic materials that will be apparent to those skilled in the art. Other adjuvants that may be included in the solvating system include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be familiar to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and rheology modifiers including thickeners and thixotropes.

The solvating system desirably is applied in at least an amount and thickness sufficient to cover the desired portion of the biofilm. It may for example be convenient to locate or make a suitable opening (e.g., a myringotomy) in the tympanic membrane so that a catheter for delivery of the solvating system may be pushed through the opening. If treatment in the inner ear is desired, a further access opening may likewise be made as noted above. The solvating system may be applied to the targeted middle ear or inner ear region and to a targeted biofilm contained therein so that the biofilm and its organisms are disrupted, solvated and subsequently removed. The treatment may involve chemical dilution or mechanical disruption. For example, the solvating system may with appropriate care be applied as a pressurized spray to dislodge the bacterial biofilm, bacteria and other foreign body buildup at the treatment site. This may be accompanied by breakdown of the biofilm EPS matrix through calcium ion sequestering by the metal ion sequestering agent, and by salvation of the resulting breakdown fragments (e.g., mannuronic and guluronic acids) into aqueous solution so as to facilitate their ultimate removal using aspiration, lavage or other removal techniques performed via the myringotomy or through the Eustachian tube or nose. It may be desirable to inject sufficient solvating system into the treatment area to displace any pus or other material that may be present, allowing excess material to overflow from the treatment area until the color of the excess material no longer changes. The solvating system may be left in place until it can drain away or is otherwise eliminated or resorbed, or the solvating system may be allowed to stand for a suitable time (e.g., a few minutes, a few hours or longer) and then may be rinsed away using saline or another suitable liquid. The solvating system preferably is applied directly into the middle or inner ear region rather than merely being applied to the ear canal and allowed to transport across the tympanic membrane, as such direct application may promote faster biofilm breakup. Application of the solvating system and removal of dislodged or disrupted biofilm and bacteria may also be repeated as desired to ensure thorough removal of the offending organisms.

The solvating system may desirably be used as a part of a multi-step treatment regimen which disrupts the bacterial biofilm and discourages its return. For example, a series of steps that may be broadly classified as Cleansing/Disrupting, Killing, Protecting/Coating, Aerating, and Healing may be carried out. The Cleansing/Disrupting step may be carried out by administering the solvating system as described above. The Killing step may be carried out by applying a suitable antimicrobial agent to the treatment site. This may for example be accomplished by including an antimicrobial agent in the solvating system or by separately applying such an agent intra operatively or post operatively (e.g., topically, orally or systemically). The Protecting/Coating step may be carried out by coating at least part of the thus-treated tissue with a protective sealant layer. The sealant may provide a variety of benefits such as discouraging or preventing recolonization of the tissue surface with bacteria and new biofilm-forming colonies; reducing inflammation; improving wound healing or allowing for the recovery of the body's natural innate immune response. The sealant may include one or more antimicrobial agents to further attack any bacterial biofilm, biofilm fragments or bacteria remaining following the Cleansing/Disrupting step described above. Further details regarding a preferred sealant may be found in copending application Ser. No. 11/739,528, filed even date herewith, the entire disclosure of which is incorporated herein by reference. The Aerating step may be carried out by preserving or forming a suitable opening or openings (e.g., a slit in the tympanic membrane) and leaving it or them open for a period of time sufficient to allow aeration of the treated ear region. The time period may be affected by the nature of the opening(s) and by whether or not a tympanostomy tube is installed. For example, if a slit has been formed in the tympanic membrane and a tube is not placed in the opening then the slit may remain open for a few days and heal over, thereby closing the ear space naturally. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal hearing or balance.

A comparable series of steps may be performed in a multistep treatment regimen which disrupts a bacterial biofilm in a sinus cavity. Further details regarding such a regimen may be found in copending application Ser. No. 11/739,480, filed even date herewith, the entire disclosure of which is incorporated herein by reference.

The invention is further illustrated in the following non-limiting examples.

Example 1

As a proxy for the S. aureus and P. aeruginosa bacteria that may be implicated in bacterial biofilms in the middle ear (other bacteria that may be implicated include S. pneumonia, H. influenzae and M. catarrhalis), bacterial isolates were recovered from the sinuses of patients with sinus disorders. Patients with cystic fibrosis or an underlying immunosuppressive disease (HIV infection, insulin-dependent diabetes mellitus, or renal disease) and patients who had taken antibiotics or oral prednisone in the previous month were excluded. All patients had refractory sinusitis, that is, persistent symptoms resistant to medical therapy despite having undergone technically successful functional endoscopic sinus surgery (FESS) for refractory chronic rhinosinusitis (CRS) with or without nasal polyposis. The occurrence of CRS was diagnosed in accordance with the 2003 American Academy of Otolaryngology-Head and Neck Surgery (AAO-HNS) guidelines set out in Benninger et al., "Adult chronic rhinosinusitis: Definitions, diagnosis, epidemiology, and pathophysiology", Otolaryngol Head Neck Surg 129(3 suppl):S1-S32 (2003). The selected patients had been refractory to medical therapy for more than 12 months before sample collection, and the failure of FESS was judged not to be associated with technical factors such as obstructive synechiae, frontal sinus obstruction, or a retained uncinate process. Samples were collected consecutively until 10 specimens each of S. aureus and P. aeruginosa were obtained using direct endoscopic guidance and the procedure described by Nadel et al., "Endoscopically guided cultures in chronic sinusitis", Am J Rhinol 12:233-241 (1998). Briefly, a topical anesthetic agent was administered, the nasal ala retracted, and an endoscope used to visualize the middle meatus and sinus cavities. A thin, flexible calcium alginate swab (STARSWAB II™ Collection and Transport System, Starplex Scientific, Etobicoke, Ontario) was inserted and directed to the site with the most purulence. If no purulence was observed, the surface of the maxillary sinus was swabbed for 15 seconds. Care was taken to avoid contact with the lateral nasal wall or nasal vestibule. Samples were plated and incubated using standard procedures. Bacteria were identified using a VITEK 2™ system (Biomörieux, Durham, N.C.). Crystal violet staining to confirm the presence of biofilms was performed according to the method described by Stepanovic et al., "A modified microtiter-plate test for quantification of staphylococcal biofilm formation", J Microbiol Methods 40:175-179 (2000). For incubation and culture, previously frozen strains were inoculated on trypticase soy agar (TSA) with 0.5% sheep blood. After 24 hours, one to four colonies per strain were cultured on TSA. Cultures were incubated at 37° C. for 24 hours to condition them to a trypticase soy broth (TSB)-TSA medium and ensure noncontamination. Colonies grown on TSA solid medium were then amplified in 5 mL of TSB medium with 0.5% glucose according to the method described by Gotz, "Staphylococcus and biofilms", Mol Microbiol 43:1367-1378 (2002) and incubated at 37° C. for at least 24 hours.

A drip-flow reactor (DFR) was used to determine the effectiveness of various test solutions delivered to S aureus and P aeruginosa biofilms on hydroxyapatite (HA)-coated microscope slides for removing these bacterial biofilms with and without hydrodynamic force. The slides in the DFR are tipped at 10° from the horizontal, thereby modeling a low shear environment. The DFR was housed in an incubator at 37° C. under aerobic conditions. Approximately 20 minutes before bacterial inoculation, sterile medium (10% TSB for S aureus; 1% TSB for P aeruginosa) was dripped on the slides in the DFR and allowed to collect over the slides to form a conditioning layer. The slides were then inoculated with 1 mL of a culture of either S aureus or P aeruginosa. The DFR was tilted so that the slides would be horizontal for 4 hours to allow bacterial attachment to the substrate. Subsequently, the DFR was set so that the slides were once again at a 10° angle, with sterile medium dripping on the slides at a rate of 10 mL per hour. After 3 days, biofilm-removal experiments were performed. Two methods were used to treat the biofilms formed by each bacterial species. The first application method involved a static treatment in the DFR, with a solvating agent (referred to as CAZS) being dripped onto the biofilms. The CAZS solvating agent contained deionized water, 25 g/L (corresponding to 0.13 M) citric acid, 5.35 g/L (corresponding to 0.02 M) caprylyl sulfobetaine zwitterionic surfactant ($CH_3(CH_2)_9N^+(CH_3)_2CH_2CH_2CH_2SO_3^-$, CAS15163-36-7) and sufficient sodium citrate (about 240 g/L) to buffer the system to pH 5.4. The second application method involved delivery of saline or delivery of CAZS outside the DFR, using a pressurized jet lavage to apply a hydrodynamic shearing force to the biofilm. For all treatments, preliminary runs were done to ensure that variations among slides were within acceptable limits. In addition, multiple plates of both bacterial species were produced to determine the within-run and run-to-run variations. A control slide was made for each DFR run. Three runs were evaluated for each treatment of each type of bacteria.

For static treatment, flow to the DFR was halted, the DFR was placed in a horizontal position, and the cover was removed. A 25 mL portion of CAZS was applied to one slide. Control slides were not treated with CAZS. After 10 minutes, the slides were rinsed with saline (25 mL). The DFR was then disconnected from the inflow tube, and each slide was removed under a laminar flow hood and placed in a sterile 50-mL tube. After another saline rinse (2 mL), the surface of the slide was scraped repeatedly, and the scrapings and saline were collected in the tube. The tube was vortexed for 10 seconds, sonicated for 2 minutes, and vortexed again for 10 seconds to disperse the bacteria into suspension. The suspensions were then serially diluted and 100-µL aliquots applied to three plates containing TSA and incubated at 37° C. for 24 hours. Colony-forming units (CFUs) were counted manually, and the number of CFUs per square centimeter was calculated. The resulting plate counts were log (10) transformed and expressed as the mean (±SD) value derived from plate counts from two DFR runs of three slides each.

For hydrodynamic treatment, the slides were removed from the DFR and placed in a glove box. The slides were placed in a holder and sprayed for approximately 20 seconds with about 150 mL of either saline or CAZS using a device that provided pressurized jet lavage. The spraying was done with both a side-to-side and an up-and-down sweeping motion so that all areas were sprayed twice, once in each axis. The slides were then placed in sterile 50-mL tubes, rinsed, scraped, dispersed, incubated and evaluated as described above.

The mean (±SD) percent reduction from control values in the quantity of *S. aureus* and *P. aeruginosa* bacteria (viz., the number of CFUs on each plate) after each treatment was calculated and the results assessed using two-sample t tests (MINITAB™ version 14, Minitab, State College, Pa.). A P value less than 0.05 was considered to represent a significant difference from the control value. The results are shown below in Table 1, expressed as the mean (±SD) number of colony-forming units per centimeter (log) derived from three plates assessed twice:

TABLE 1

Bacterial Plate Log Counts According to Type of Treatment

| Treatment | Staphylococcus aureus | Pseudomonas aeruginosa |
| --- | --- | --- |
| None (Control) | 8.7 ± 0.4 | 9.2 ± 0.2 |
| Static CAZS delivery | 6.2 ± 0.3 | 6.3 ± 1.3 |
| Hydrodynamic saline delivery | 6.4 ± 0.2 | 6.9 ± 0.1 |
| Hydrodynamic CAZS delivery | 4.8 ± 0.3 | 4.0 ± 0.5 |

The results in Table 1 show that significant bacterial biofilm removal was obtained. Before treatment, ample biofilms formed in the DFR cultures of both *S. aureus* and *P. aeruginosa*, with CFU counts for these Controls ranging from 7.8 to 9.5 log/cm$^2$. Static administration of CAZS resulted in a 2.5 log reduction ($5.11 \times 10^8$ to $1.65 \times 10^6$; P 0.001) in the number of *S. aureus* CFUs and a 2.9 log reduction ($1.69 \times 10^9$ to $1.91 \times 10^6$; P=0.002) in the number of *P. aeruginosa* CFUs. Mechanical disruption using hydrodynamic saline delivery alone decreased the number of *S. aureus* CFUs by 2.3 log units ($5.11 \times 10^8$ to $2.38 \times 10^6$; P=0.001) and the number of *P. aeruginosa* CFUs by 2.4 log units ($1.69 \times 10^9$ to $7.31 \times 10^6$; P=0.001). However, mechanical disruption using hydrodynamic CAZS decreased the *S. aureus* CFU count by 3.9 log units ($5.11 \times 10^8$ to $6.37 \times 10^4$; P=0.001) and the *P. aeruginosa* CFU count by 5.2 log units ($1.69 \times 10^9$ to $1.04 \times 10^4$; P=0.001).

Confocal scanning laser microscopy (CSLM) was performed on three slides (for each treatment and bacteria species) not subjected to plate counts to allow imaging of the biofilm architecture in control and treated samples. The slides were stained for CSLM using a BACLIGHT™ Live/Dead kit (Molecular Probes, Invitrogen, Carlsbad, Calif.) containing two nucleic acid stains (SYTO 9, which detects living cells by fluorescing green, and propidium iodide, which detects dead cells by fluorescing red). After staining, the slides were examined using CSLM at a 630× magnification using a LEICA™ SP2 acoustic-optical beam splitter with a 2-photon MAI TAI™ attachment (Leica Microsystems, Bannockburn, Ill.) and fluorescence excitation and detection in both the green and red spectra. Each slide area was divided into 10 equally sized segments. A microscopic field was selected at random from each segment, and images were obtained at 1-µm intervals from the top of the biofilm to the substrate, thereby creating an image stack for each location. The CSLM analysis revealed that a thick biofilm carpeted the Control slides. Hydrodynamic treatment with saline and static treatment with CAZS decreased the amount of biofilm coverage markedly and reduced the organization of the remaining biofilm. Hydrodynamic treatment with CAZS produced a greater reduction both in biofilm coverage and in the amount of order in the biofilm community. The results corresponded generally to the plate count assessments with respect to the relative reductions in the amount of biofilm achieved with each treatment.

Of the three treatments investigated, power irrigation using CAZS and a pressurized jet lavage was the most effective in disrupting the bacterial biofilms. Power irrigation using saline had appreciable biofilm-reducing effects. However, the presence of a surfactant and citric acid in the irrigation solution significantly enhanced the reduction in CFU count in both *S. aureus* and *P. aeruginosa* biofilms. Large, statistically significant reductions occurred, with the mean decreases in bacterial plate counts being 3.9 and 5.2 log (a reduction of 10,000 to 100,000 times), respectively, for *S. aureus* and *P. aeruginosa* biofilms. A decrease of this magnitude in vitro indicates that an appropriate in vivo treatment in the middle or inner ear should effectively disrupt bacterial biofilms found there. Any remaining low level of persistent bacterial infection might be dealt with by host defenses or a topically or orally administered antimicrobial agent, and by application of a sealant as described above.

Example 2

The CAZS solvating system employed in Example 1 was modified by replacing some of the water with gallium nitrate so that the modified system contained 25% gallium nitrate. A Control solution containing 25% gallium nitrate in deionized water was also prepared. When evaluated using the static treatment technique of Example 1, administration of the gallium nitrate Control solution resulted in a 3.4 log reduction (average of 4 runs) in the number of *S. aureus* CFUs and a 4.1 log reduction (average of 3 runs) in the number of *P. aeruginosa* CFUs. Static administration of the solution containing CAZS and gallium nitrate resulted in a 5.2 log reduction (average of 2 runs) in the number of *S. aureus* CFUs and a 5.5 log reduction (average of 2 runs) in the number of *P. aeruginosa* CFUs.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

We claim:

1. A method for treating chronic otitis media and other bacterial ear conditions, which method comprises:
    a) applying an aqueous solvating system comprising a metal ion sequestering agent and greater than 0.2 wt. % cationic or zwitterionic surfactant to a bacterial biofilm comprising an extracellular polysaccharide matrix attached or adhered to at least a portion of the middle or inner ear,
    b) detaching, removing or otherwise disrupting at least a part of the biofilm by solvating the extracellular polysaccharide matrix with the solvating system, and then
    c) rinsing away the solvating system.

2. A method according to claim 1 wherein the solvating system is applied to at least a portion of the middle ear.

3. A method according to claim 1 comprising applying the solvating system by spraying, lavage, misting, mopping, wicking or dripping.

4. A method according to claim 1 wherein the metal ion sequestering agent comprises a mild acid whose acidity is sufficient to sequester one or more metal ions in the bacteria biofilm but which is not so acidic so as to harm the middle or inner ear portion to which the solvating system is applied.

5. A method according to claim 1 wherein the metal ion sequestering agent comprises a sequestering agent for sodium, calcium or iron.

6. A method according to claim 1 wherein the metal ion sequestering agent comprises a carboxylic acid, diacid, triacid or mixture thereof.

7. A method according to claim 6 wherein the metal ion sequestering agent comprises formic acid, acetic acid, chloroacetic acid, dichloroacetic acid, oxalic acid, oxamic acid, glycolic acid, lactic acid, pyruvic acid, aspartic acid, fumaric acid, maleic acid, succinic acid, iminodiacetic acid, glutaric acid, 2-ketoglutaric acid, glutamic acid, adipic acid, glucuronic acid, mucic acid, nitrilotriacetic acid, salicylic acid, ketopimelic acid, benzoic acid, mandelic acid, chloromandelic acid, phenylacetic acid, phthalic acid, boric acid or mixture thereof.

8. A method according to claim 6 wherein the metal ion sequestering agent comprises citric acid.

9. A method according to claim 1 wherein the surfactant comprises a zwitterionic surfactant.

10. A method according to claim 1 wherein the metal ion sequestering agent is present at a concentration of about 0.01 to about 0.5 M.

11. A method according to claim 1 wherein the surfactant is about 0.3% to about 30% of the solvating system.

12. A method according to claim 1 wherein the solvating system further comprises sufficient buffer so that the solvating system has a pH greater than 5.

13. A method according to claim 1 wherein the solvating system further comprises an antimicrobial agent.

14. A method for treating chronic otitis media and other bacterial ear conditions, which method comprises:
 a) applying an aqueous solvating system comprising a metal ion sequestering agent, a cationic or zwitterionic surfactant, and sufficient buffer so that the solvating system has a pH greater than 5 to a bacterial biofilm comprising an extracellular polysaccharide matrix attached or adhered to at least a portion of the middle or inner ear,
 b) detaching, removing or otherwise disrupting at least a part of the biofilm by solvating the extracellular polysaccharide matrix with the solvating system, and then
 c) rinsing away the solvating system.

15. A method according to claim 14 wherein the metal ion sequestering agent comprises a carboxylic acid, diacid, triacid or mixture thereof.

16. A method according to claim 15 wherein the metal ion sequestering agent comprises formic acid, acetic acid, chloroacetic acid, dichloroacetic acid, oxalic acid, oxamic acid, glycolic acid, lactic acid, pyruvic acid, aspartic acid, fumaric acid, maleic acid, succinic acid, iminodiacetic acid, glutaric acid, 2-ketoglutaric acid, glutamic acid, adipic acid, glucuronic acid, mucic acid, nitrilotriacetic acid, salicylic acid, ketopimelic acid, benzoic acid, mandelic acid, chloromandelic acid, phenylacetic acid, phthalic acid, boric acid or mixture thereof.

17. A method according to claim 15 wherein the metal ion sequestering agent comprises citric acid.

18. A method according to claim 14 wherein the solvating system has a pH greater than 5 and less than 8.5.

19. A method according to claim 14 wherein the solvating system further comprises an antimicrobial agent.

20. A solvating system comprising an aqueous composition containing a metal ion sequestering agent, greater than 0.2 wt. % cationic or zwitterionic surfactant, and an antimicrobial agent, and wherein the composition is on a biofilm comprising an extracellular polysaccharide matrix disposed on tissue within the middle or inner ear and contains sufficient metal ion sequestering agent and sufficient surfactant to solvate such an extracellular polysaccharide matrix.

21. A solvating system according to claim 20 wherein the metal ion sequestering agent comprises a mild acid whose acidity is sufficient to sequester one or more metal ions in the extracellular polysaccharide matrix but which is not so acidic so as to harm the middle or inner ear portion to which the solvating system is applied.

22. A solvating system according to claim 20 wherein the metal ion sequestering agent comprises a sequestering agent for sodium, calcium or iron.

23. A solvating system according to claim 20 wherein the metal ion sequestering agent comprises a carboxylic acid, diacid, triacid or mixture thereof.

24. A solvating system according to claim 23 wherein the metal ion sequestering agent comprises formic acid, acetic acid, chloroacetic acid, dichloroacetic acid, oxalic acid, oxamic acid, glycolic acid, lactic acid, pyruvic acid, aspartic acid, fumaric acid, maleic acid, succinic acid, iminodiacetic acid, glutaric acid, 2-ketoglutaric acid, glutamic acid, adipic acid, glucuronic acid, mucic acid, nitrilotriacetic acid, salicylic acid, ketopimelic acid, benzoic acid, mandelic acid, chloromandelic acid, phenylacetic acid, phthalic acid, boric acid or mixture thereof.

25. A solvating system according to claim 23 wherein the metal ion sequestering agent comprises citric acid.

26. A solvating system according to claim 20 wherein the surfactant comprises a zwitterionic surfactant.

27. A solvating system according to claim 20 wherein the surfactant comprises a cationic surfactant.

28. A solvating system according to claim 20 wherein the antimicrobial agent comprises a chitosan salt, cubic-phase lipid, gallium-containing compound, carboxylic ester, sulfonic acid, active halogen compound, active oxygen compound, organic peroxide, ozone, singlet oxygen generator, phenolic derivative or quaternary ammonium compound.

29. A solvating system according to claim 20 wherein the antimicrobial agent comprises gallium acetoacetonate, gallium bromide, gallium chloride, gallium fluoride, gallium iodide, gallium maltolate, gallium nitrate, gallium nitride, gallium percolate, gallium phosphite, gallium sulfate or mixture thereof.

30. A solvating system according to claim 20 wherein the metal ion sequestering agent is present at a concentration of about 0.01 to about 0.5 M.

31. A solvating system according to claim 20 wherein the surfactant is about 0.5% to about 25% of the solvating system.

32. A solvating system according to claim 20 wherein the solvating system further comprises sufficient buffer so that the solvating system has a pH greater than 5.

33. A solvating system according to claim 32 wherein the solvating system has a pH less than 8.5.

34. A solvating system comprising an aqueous composition containing a metal ion sequestering agent, a cationic or zwitterionic surfactant and sufficient buffer so that the solvating system has a pH greater than 5, and wherein the composition is on a biofilm comprising an extracellular polysaccharide matrix disposed on tissue within the middle or inner ear and contains sufficient metal ion sequestering agent and sufficient surfactant to solvate such an extracellular polysaccharide matrix.

35. A solvating system according to claim 34 wherein the metal ion sequestering agent comprises a carboxylic acid, diacid, triacid or mixture thereof.

36. A solvating system according to claim 35 wherein the metal ion sequestering agent comprises formic acid, acetic acid, chloroacetic acid, dichloroacetic acid, oxalic acid, oxamic acid, glycolic acid, lactic acid, pyruvic acid, aspartic acid, fumaric acid, maleic acid, succinic acid, iminodiacetic acid, glutaric acid, 2-ketoglutaric acid, glutamic acid, adipic acid, glucuronic acid, mucic acid, nitrilotriacetic acid, salicylic acid, ketopimelic acid, benzoic acid, mandelic acid, chloromandelic acid, phenylacetic acid, phthalic acid, boric acid or mixture thereof.

37. A solvating system according to claim 35 wherein the metal ion sequestering agent comprises citric acid.

38. A solvating system according to claim 34 wherein the solvating system has a pH less than 8.5.

39. A solvating system according to claim 34 wherein the solvating system further comprises an antimicrobial agent.

40. A solvating system according to claim 39 wherein the antimicrobial agent comprises gallium acetoacetonate, gallium bromide, gallium chloride, gallium fluoride, gallium iodide, gallium maltolate, gallium nitrate, gallium nitride, gallium percolate, gallium phosphite, gallium sulfate or mixture thereof.

41. A solvating system according to claim 34 wherein the surfactant comprises a cationic surfactant.

42. A solvating system according to claim 34 wherein the surfactant comprises a zwitterionic surfactant.

43. A solvating system according to claim 34 further comprising a steroid.

44. A method according to claim 14 wherein the surfactant comprises a cationic surfactant.

45. A method according to claim 14 wherein the surfactant comprises a zwitterionic surfactant.

46. A method according to claim 1 wherein the surfactant comprises a cationic surfactant.

* * * * *